(12) United States Patent
Aranyi et al.

(10) Patent No.: US 7,652,021 B2
(45) Date of Patent: Jan. 26, 2010

(54) COMPOUNDS USEFUL FOR DPP-IV ENZYME INHIBITION

(75) Inventors: Peter Aranyi, Budapest (HU); Imre Bata, Budapest (HU); Sandor Batori, Budapest (HU); Eva Boronkay, Budapest (HU); Philippe Bovy, Mareil Marly (FR); Zoltan Kapui, Budapest (HU); Edit Susan, Dunakeszi (HU); Tibor Szabo, Budapest (HU); Katalin Urban-Szabo, Budapest (HU); Marton Varga, Dunakeszi (HU)

(73) Assignee: Sanofi-Aventis, Paris (FR)

( * ) Notice: Subject to any disclaimer, the term of this patent is extended or adjusted under 35 U.S.C. 154(b) by 16 days.

(21) Appl. No.: 11/364,154

(22) Filed: Feb. 28, 2006

(65) Prior Publication Data

US 2006/0276487 A1    Dec. 7, 2006

Related U.S. Application Data

(63) Continuation of application No. PCT/HU2004/000088, filed on Aug. 27, 2004.

(30) Foreign Application Priority Data

Aug. 29, 2003   (HU) .................................. 0302788

(51) Int. Cl.
*C07D 403/12* (2006.01)
*C07D 401/12* (2006.01)
*C07D 409/12* (2006.01)
*C07D 413/12* (2006.01)
*C07D 417/12* (2006.01)
*C07D 471/04* (2006.01)
*A61K 31/506* (2006.01)
*A61K 31/33* (2006.01)
*A61K 31/41* (2006.01)
*A61P 3/10* (2006.01)

(52) U.S. Cl. ................. 514/272; 514/275; 514/252.01; 514/300; 514/313; 514/336; 514/370; 514/378; 514/403; 544/320; 544/330; 544/238; 548/161; 548/245; 548/364.1

(58) Field of Classification Search ................ 544/320, 544/330, 238; 514/272, 275, 252.01, 300, 514/313, 336, 370, 378, 403; 546/268.1, 546/152, 117; 548/161, 245, 364.1

See application file for complete search history.

(56) References Cited

FOREIGN PATENT DOCUMENTS

| EP | 1323710 | 7/2003 |
|---|---|---|
| WO | WO 01/34594 | 5/2001 |
| WO | WO 01/81337 | 11/2001 |
| WO | WO 02/051836 | 7/2002 |
| WO | WO 03/002553 | 1/2003 |
| WO | WO 03/037904 | 5/2003 |
| WO | WO 03/074500 | 9/2003 |
| WO | WO 03/106456 | 12/2003 |

OTHER PUBLICATIONS

West, Anthony R., Solid State Chemistry and its Applications, Wiley, New York, 1988, pp. 358 & 365.*
Vippagunta et al., Advanced Drug Delivery Reviews 48: 3-26, 2001.*
Cecil Textbook of Medicine, edited by Bennet, J.C., and Plum F., 20th edition,vol. 1, 1004-1010, 1996.*
Green et al., Expert Opin. Emerging Drugs, 11(3); 525-539, 2006.*
Conti, S., et. al., Chiral Ligands Containing Heteroatoms:13.1 Optically Active 4-(2'-Pyridyl)- 1,3-Oxazolidines: an Improved Synthesis of 2-(2'-Pyridyl)-2-Aminoalcohols, Tetrahedron vol. 50, No. 47, pp. 13493-13500 (1994).
Demange, L., et. al., Practical Synthesis of Boc and Fmoc Protected 4-Fluoro and 4-Difluoroprolines from Trans-4-Hydroxyproline, Tetrahedron Letters 39 (1998) pp. 1169-1172.
Lavrova, L.N., et. al., Synthesis and Biological Activity of Some 1-Hydroxy-3- Aminoalkyladamantanes and Their Derivatives, Pharm. Chem. J. (Engl. Trans.) (1990) vol. 24, pp. 35-39.
Lowe, J.A., et. al., Aza-Tricyclic Substance P Antagonists, J. Med. Chem. (1994) vol. 37, pp. 2831-2840.
Mark Taylor, G., et. al., On the Ritter Reaction of Cyclic Hydroxyamines: Synthesis of Conformationally-Restricted Reduced Amide Dipeptide Isosteres, Tetrahedron Letters, vol. 37, No. 8, pp. 1297-1300 (1996).
Momose, T., et. al., Bicyclo[3.3.1]Nonanes as Synthetic Intermediates. Part 19.1 Asymmetric Cleavage of omega-Azabicyclo[3.n.1]Alkan-3-Ones at the 'Fork Head', J. Chem. Soc. Perkin Trans. 1, (1997) pp. 1307-1313.
Prelog, V., et. al., Uber eine neue, ergiebigere darstellung des Adamantans, Berichte (1941), 74, 1769.

* cited by examiner

*Primary Examiner*—Venkataraman Balasubramanian
(74) *Attorney, Agent, or Firm*—Barbara Kurys

(57) ABSTRACT

The present invention relates to the novel compounds of the general formula (I) possessing dipeptidyl peptidase IV enzyme inhibitory activity, pharmaceutical compositions thereof, methods of using said compounds, processes for their preparation and intermediates of the general formulae (II), (IV), (V), (VII), (VIII) and (IX).

5 Claims, No Drawings

COMPOUNDS USEFUL FOR DPP-IV ENZYME INHIBITION

SUMMARY OF THE INVENTION

The present invention relates to the novel compounds of the general formula (I) possessing dipeptidyl peptidase IV enzyme inhibitory activity, as well as their salts, solvates and isomers, to the pharmaceutical compositions containing them, to the therapeutic application of the compounds of the general formula (I), to the process of preparation of the compounds of the general formula (I) and to the new intermediates of the general formulae (II), (IV), (V), (VII), (VIII) and (IX).

BACKGROUND OF THE INVENTION

The enzyme, dipeptidyl peptidase IV (DPP-IV), which is identical with the lymphocyte surface glycoprotein CD26, a polypeptide with the molecular mass of 110 k Dalton, is formed in the tissues and organs of mammals. This enzyme can be found, among others, in the liver, in the Langerhans islands, in the renal cortex, in the lungs, and in certain tissues of the prostate and small intestine. Significant DPP-IV activity can be observed furthermore in the body liquors (as for instance in the plasma, serum and urine). DPP-IV is a serine protease type enzyme, which has the unique specificity to cleave dipeptides from the N-terminals of the peptides, where the pre-terminal dipeptide is prolyl-alanine, or hydroxy-proline.

DPP-IV enzyme is responsible for the decomposition of the glucagon-like peptides, peptide-1 (GLP-1) and peptide-2 (GLP-2) in the body. The enzyme GLP-1 strongly stimulates the insuline production of the pancrease, thus it has a direct, favourable effect on the glucose homeostasis, therefore DPP-IV inhibitors are suitable for the treatment of non-insuline dependent diabetes mellitus (NIDDM) and for the treatment or prophylaxis of other diseases connected to the DPP-IV enzyme activity, including but not limited to diabetes, obesity, hyperlipidemia, dermatological or mucous membrane disorders, psoriasis, intestinal distress, constipation, autoimmune disorders such as encephalomyelitis, complement metiated disorders such as glomerulonephritis, lipodystrohy and tissue damage, psychosomatic, depressive and neuropsychiatric disease such as anxiety, depression, insomnia, schizophrenia, epilepsy, spasm and chronic pain, HIV infection, allergies, inflammation, arthritis, transplant rejection, high blood pressure, congestive heart failure, tumors and stress-induced abortions. There are a number of DPP-IV inhibitors known in the literature, but they have disadvantages as regards their activity, toxicity, physico-chemical properties, stability and duration of action.

Our aim was to prepare new, effective and safe DPP-IV inhibitors having advantageous physico-chemical and biological properties.

DETAILED DESCRIPTION OF THE INVENTION

We have found that the compounds of the general formula (I)

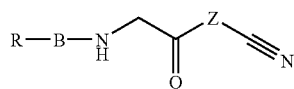

(I)

wherein R represents:
a nitrogen-containing mono- or bicyclic aromatic moiety, preferably pyridyl, pyridazinyl, pyrimidinyl, pyrazinyl, imidazolyl, pirazolyl, thiazolyl, isothiazolyl, oxazolyl, isoxazolyl, oxadiazolyl, tetrazinyl, triazinyl, quinolinyl, isoquinolinyl, cinnolinyl, phthalazinyl, quinazolinyl, quinoxalinyl, benzimidazolyl, indazolyl, benzothiazolyl, benzisothiazolyl, benzoxazolyl or benzisoxazolyl moiety; optionally mono- or disubstituted independently by one or two of the following groups: C1-4 alkyl group, C1-4 alkoxy group, C2-5 alkoxycarbonyl group, halogen atom, trihalogenomethyl group, methylthio group, nitro group, carboxamido group, cyano group; or Phenyl group, which is mono- or disubstituted, independently by one or two of the following groups: C1-4 alkyl group, C1-4 alkoxy group, C1-4 alkylenedioxy group, trihalogenomethyl group, methylthio group, nitro group, cyano group, C2-5 alkylcarbonyl group, C2-5 alkoxycarbonyl group, C2-8 dialkylamino group; or $R_{1a}$—$CH_2$-group, where the meaning of $R_{1a}$ is hydrogen, C1-4 alkyl group, pheny, benzyl, phenylethyl, phenylethenyl, naphthyl, pyridyl, quinolyl, isoquinolyl, cinnolinyl, phthalazyl, quinazolinyl, quinoxalinyl, thienyl, furyl or p-tolylsulphonyl group, substituted independently by one or more C1-4 alkyl, C1-4 alkoxy, alkylenedioxy group, halogen atom, trihalogenomethyl, nitro or cyano group; or $R^{1a}R^2$—CH group, where
the meaning of $R^{1a}$ is C1-4 alkyl group, phenyl, benzyl, phenylethyl, phenylethenyl, fenylpropyl, naphthyl, pyridyl, quinolyl, isoquinolyl, cinnolinyl, phthalazyl, quinazolinyl, quinoxalinyl, thienyl, or furyl group, substituted independently with one or more C1-4 alkyl, C1-4 alkoxy, C1-4 alkylenedioxy, halogeno, trihalogenomethyl, nitro, amino or cyano group, or a phenylcarbonyl moiety, substituted independently with one or more, C1-4 alkyl, -alkoxy, -alkylenedioxy halogeno, trihalogenomethyl, nitro-, amino- or cyano group, and $R^2$ represents hydrogen or methyl group; or $R^{1b}$—CO group, where
the meaning of $R^{1b}$ is C1-4 alkyl group, or a phenyl, benzyl, phenylethyl, phenylethenyl, naphthyl, pyridyl, quinolyl, isoquinolyl, cinnolinyl, phthalazyl, quinazolinyl, quinoxalinyl moiety, substituted independently with one or more C1-4 alkyl, C1-4 alkoxy, C1-4 alkylenedioxy, halogeno, trihalogenomethyl, nitro, or cyano group, or an amino group, or a heterocyclic group, preferably pyrrolidino, piperidino, piperazino, morpholino, thienyl or furyl group; or p-toluenesulphonyl group;
B represents a group of formula (1), (2), (3), (4) or (5);

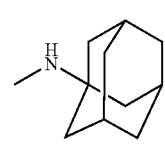

(1)

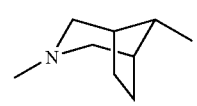

(2)

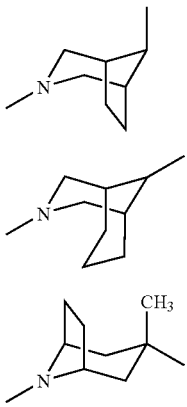

(3)

(4)

(5)

Z represents a group of formula (A), (B), (C), (D) or (E),

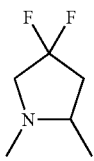

(A)

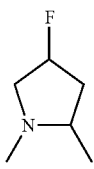

(B)

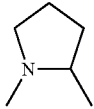

(C)

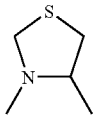

(D)

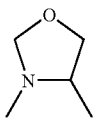

(E)

and isomers, salts, solvates of the above compounds, as well as solvates of their salts, possess remarkable advantages in their activity, stability and toxicity. In accordance with the accepted terminology, the configuration of the carbon atom next to the nitrogen atom of the 5-membered-ring-pentacycle is favourably S if Z stands for formula (A), (B), (C), or (E), whereas it is favourably R if Z stands for formula (D).

In the present description the term "$C_{1-4}$ alkyl" means a straight-chain or branched chain alkyl group with 1-4 carbon atoms as for example methyl, ethyl, propyl, isopropyl, butyl, sec.-butyl or isobutyl.

The term "$C_{1-4}$ alkoxy" means a straight-chain or branched chain alkoxy group with 1-4 carbon atom as for example methoxy, ethoxy, propoxy, isopropoxy, butoxy, sec.-butoxy or isobutoxy.

The term "$C_{2-5}$ alkoxy carbonyl" means a straight or branched chain alkoxy carbonyl group with 2-5 carbon atom as for example methoxy carbonyl, ethoxy carbonyl, popoxy carbonyl, isopropoxy carbonyl, butoxy carbonyl, sec.-butoxy carbonyl, isobutoxy carbonyl.

The term "halogen" means fluorine, chlorine, bromine or iodine.

The term "$C_{1-4}$ alkylenedioxy" means a straight-chain or branched chain alkylenedioxy group with 1-4 carbon atoms as for example methylenedioxy, ethylenedioxy, propxylenedioxy, butylenedioxy.

The term "$C_{2-5}$ alkylcarbonyl" menas a straight-chain or branched chain alkylcarbonyl group with 2-5 carbon atoms as for example methyl-carbonyl, ethylcarbonyl, propylcarbonyl, isopropyl carbonyl or butyl carbonyl, sec.-butyl carbonyl or isobutyl carbonyl.

All references given below to "compound(s) of formula I" refer to compound(s) of the formula I as described above, and also to their salts, solvates and physiologically functional derivatives as described herein. The term "physiologically functional derivative" used herein refers to any physiologically tolerated derivative of a compound of the formula I according to the invention, e.g. an ester which is able, on administration to a mammal, e.g. a human, to (directly or indirectly) form a compound of the formula I or an active metabolite thereof. The physiologically functional derivatives also include prodrugs of the compounds according to the invention, for example as described in H. Okada et al., Chem. Pharm. Bull. 1994, 42, 57-61. Such prodrugs can be metabolized in vivo to a compound according to the invention. These prodrugs may or may not be active themselves.

In addition, the term "compound(s) of formula I" is understood to refer to racemates, racemic mixtures and pure enantiomers, and also to their diastereomers and mixtures thereof.

The compounds according to the invention can also exist in different polymorphous forms, for example as amorphous and crystalline polymorphous forms. All polymorphous forms of the compounds according to the invention are encompassed by the scope of the invention and are a further aspect of the invention.

A large group of compounds of the general formula (I) are -wherein the meaning of R is the same as defined earlier, B represents a group of formula (1), (2), (4) or (5) and Z represents a group of formula (A), (B) or (D).

Such compounds from this large group are for instance
(2S)-4,4-difluoro-1-{N-[3-(pyrimidin-2-ylamino)-1-adamantyl]glycyl}pyrrolidine-2-carbonitrile
(2S)-4,4-difluoro-1-(N-{3-[(3-nitrobenzyl)amino]-1-adamantyl}glycyl)pyrrolidine-2-carbonitrile
N-(3-{[2-(2-cyano-(2S)-4,4-difluoropyrrolidin-1-yl)-2-oxoethyl]amino}-1-adamantyl)-4-methoxybenzamide
(2S)-4,4-difluoro-1-[N-(3-pyrimidin-2-yl-3-azabicyclo[3.2.1]oct-8-yl)exo-aminoacetyl]pyrrolidine-2-carbonitrile
(2S)-4,4-difluoro-1-[N-(3-pyrimidin-2-yl-3-azabicyclo[3.2.1]oct-8-yl)endo-aminoacetyl]pyrrolidine-2-carbonitrile
(2S)-4,4-difluoro-1-[N-(3-methyl-8-pyrimidin-2-yl-8-azabicyclo[3.2.1]oct-3-yl) exo-aminoacetyl]pyrrolidine-2-carbonitrile
(2S,4S)-4-fluoro-1-{N-[3-(pyrimidin-2-ylamino)-1-adamantyl]glycyl}pyrrolidine-2-carbonitrile
(4R)-3-{N-[3-(pyrimidin-2-ylamino)-1-adamantyl]glycyl}-1,3-thiazolidine-4-carbonitrile
(4S)-3-{N-[3-(pyrimidin-2-ylamino)-1-adamantyl]glycyl}-1,3-oxazolidine-4-carbonitrile
(2S)-4,4-difluoro-1-{N-[3-(1,2,4-triazin-3-ylamino)-1-adamantyl]glycyl}pyrrolidine-2-carbonitrile (2S)-4,4-difluoro-1-{N-[3-(pyrazin-2-ylamino)-1-adamantyl]glycyl}pyrrolidine-2-carbonitrile
(2S)-1-(N-{3-[(4-cyanophenyl)amino]-1-adamantyl}glycyl)-4,4-difluoropyrrolidine-2-carbonitrile
6-[(3-{[2-(2-cyano-(2S)-4,4-difluoropyrrolidin-1-yl)-2-oxoethyl]amino}-1-adamantyl)amino]nicotinonitrile
(2S)-4,4-difluoro-1-[N-(3-{[5-(trifluoromethyl)pyridin-2-yl]amino}-1-adamantyl)glycyl]pyrrolidine-2-carbonitrile
(2S,4S)-4-fluoro-1-[N-(3-{[5-(trifluoromethyl)pyridin-2-yl]amino}-1-adamantyl)glycyl]pyrrolidine-2-carbonitrile
(2S)-4,4-difluoro-1-{N-[3-(1,3-thiazol-2-ylamino)-1-adamantyl]glycyl}pyrrolidine-2-carbonitrile
(2S)-1-(N-{3-[(1-ethyl-1H-pyrazol-5-yl)amino]-1-adamantyl}glycyl)-4,4-difluoropyrrolidine-2-carbonitrile
(2S)-4,4-difluoro-1-(N-{3-[(5-methylisoxazol-3-yl)amino]-1-adamantyl}glycyl) pyrrolidine-2-carbonitrile
(2S)-4,4-difluoro-1-{N-[3-(quinolin-2-ylamino)-1-adamantyl]glycyl}pyrrolidine-2-carbonitrile
(2S,4S)-4-fluoro-1-{N-[3-(quinolin-2-ylamino)-1-adamantyl]glycyl}pyrrolidine-2-carbonitrile
(2S)-4,4-difluoro-1-{N-[3-([1,2,4]triazolo[1,5-a]pyridin-2-ylamino)-1-adamantyl]glycyl}pyrrolidine-2-carbonitrile
(2S,4S)-4-fluoro-1-{N-[3-([1,2,4]triazolo[1,5-a]pyridin-2-ylamino)-1-adamantyl]glycyl}pyrrolidine-2-carbonitrile
(4R)-3-{N-[3-([1,2,4]triazolo[1,5-a]pyridin-2-ylamino)-1-adamantyl]glycyl}-1,3-thiazolidine-4-carbonitrile
(2S)-1-(N-{3-[(4-cyanobenzyl)amino]-1-adamantyl}glycyl)-4,4-difluoropyrrolidine-2-carbonitrile
(2S)-4,4-difluoro-1-[N-(3-{[4-(trifluoromethyl)benzyl]amino}-1-adamantyl) glycyl]pyrrolidine-2-carbonitrile
(2S)-4,4-difluoro-1-(N-{3-[(3-fluorobenzyl)amino]-1-adamantyl}glycyl)pyrrolidine-2-carbonitrile
(2S)-4,4-difluoro-1-(N-{3-[(3,4,5-trimethoxybenzyl)amino]-1-adamantyl}glycyl)pyrrolidine-2-carbonitrile
(2S)-4,4-difluoro-1-(N-{3-[(pyridin-3-ylmethyl)amino]-1-adamantyl}glycyl)pyrrolidine-2-carbonitrile
(2S)-4,4-difluoro-1-(N-{3-[(pyridazin-3-ylmethyl)amino]-1-adamantyl}glycyl)pyrrolidine-2-carbonitrile
(2S)-4,4-difluoro-1-(N-{3-[(1,3-thiazol-2-ylmethyl)amino]-1-adamantyl}glycyl) pyrrolidine-2-carbonitrile
4-chloro-N-(3-{[2-(2-cyano-(2S)-4,4-difluoropyrrolidin-1-yl)-2-oxoethyl]amino}-1-adamantyl)benzamide
N-(3-{[2-(2-cyano-(2S)-4,4-difluoropyrrolidin-1-yl)-2-oxoethyl]amino}-1-adamantyl)-3-fluorobenzamide
(2E)-N-(3-{[2-(2-cyano-(2S)-4,4-difluoropyrrolidin-1-yl)-2-oxoethyl]amino}-1-adamantyl)-3-phenylacrylamide
N-(3-{[2-(2-cyano-(2S)-4,4-difluoropyrrolidin-1-yl)-2-oxoethyl]amino}-1-adamantyl)thiophene-2-carboxamide
(2S)-1-[N-(3-pyrimidin-2-yl-3-azabicyclo[3.2.1]oct-8-yl) endo-amino-acetyl]pyrrolidine-2-carbonitrile
(2S)-4,4-difluoro-1-[N-(3-pyrimidin-2-yl-3-azabicyclo[3.3.1]non-9-yl)glycyl]pyrrolidine-2-carbonitrile
6-(9-{[2-(2-cyano-(2S)-4,4-difluoropyrrolidin-1-yl)-2-oxoethyl]amino}-3-azabicyclo[3.3.1]non-3-yl)pyridazine-3-carbonitrile
(2S)-1-[N-(3-pyrimidin-2-yl-3-azabicyclo[3.3.1]non-9-yl) glycyl]pyrrolidine-2-carbonitrile The compounds of the general formula (I) according to our invention—wherein the meanings of R, B and Z are as defined above—can be prepared by alkylation of the cyclic primary amines of the general formula (II)

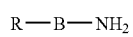

(II)

with the chloroacetyl derivatives of general formula (III)

(III)

wherein the meaning of Z is as defined above—and, if desired, the resulting compounds are transformed into their salts or solvates (Scheme 1).

In the course of the alkylation the cyclic primary amines of the general formula (II) are applied in equivalent amount or in slight excess, and the resulting hydrogen chloride is bound by various acid binding agents, preferably by a base, such as for instance triethylamine, potassium carbonate, 1,8-diazabicyclo[5.4.0]undec-7-ene (DBU), or scavenger resin, polimer bound 2-tert-butylimino-2-diethylamino-1,3-dimethyl-perhydro-1,3,2-diazaphosphorine (PBEMP), polemic bound diethylamine (PS-DIEA).

The reaction is generally performed at a temperature between 25 and 75° C. in acetonitrile, alcoholes, tetrahydrofuran or dioxane.

The primary amines of the general formula (II)—if moiety B stands for formula (2), (3), (4) or (5)—are prepared in a two-step synthesis (Scheme 2). In the first step the starting cyclic secondary amines containing the acylamido sidechain—the compound of the general formula (IV)

(IV)

wherein Y stands for acetyl or tert-butoxycarbonyl group—is reacted with the compound containing the group R, forming thus the compunds of general formula (V).

(V)

If R means aryl or hetaryl group, aryl or hetaryl halogenides, preferably aryl- or hetaryl bromides or aryl- or hetaryl chlorides are used for the arylation reaction. The arylation is performed in a polar, protic or aprotic solvent between 70 and 140° C., generally in an alcohol (ethanol, n-butanol, n-pentanol), or in microwave oven without solvent, using excess amine or DBU as acid binder. The arylation is also performed in an aprotic or polar solvent, at a temperature between 25 and 110° C., preferably in toluene or in dimethoxyethane, using sodium alcoholates as acid binders and palladium complexes as catalysts (J. Org. Chem. 2000, 65, 1158).

In the cases when R stands for $R^{1a}R^2$—CH— or $R^{1b}$—CO group, the compounds of the general formula (IV)—wherein Y means an acetyl or tert-butoxycarbonyl group—are reacted with the derivatives of general formula $R^{1a}R^2$—CHX or $R^{1b}$—COX—wherein X means a leaving group (preferably a chloro- or bromo atom)—generally at a temperature around 0° C., using an inorganic or organic base, preferably triethylamine, as acid binder.

The compounds of the general formula (IV), by literature analogy, are prepared in several steps. If moiety (B) stands for the group of formula (2) or (3), the starting material is the 3-benzyl-3-azabicyclo[3.2.1]octan-8-one (N-benzylcamphidin-8-one; J. Med. Chem. 1994, 37, 2831). From that, the desired compound is prepared in four steps. The isomeric products obtained in the second step are separated by coloumn chromatography for the exo and endo products, which further on are reacted in the same way:

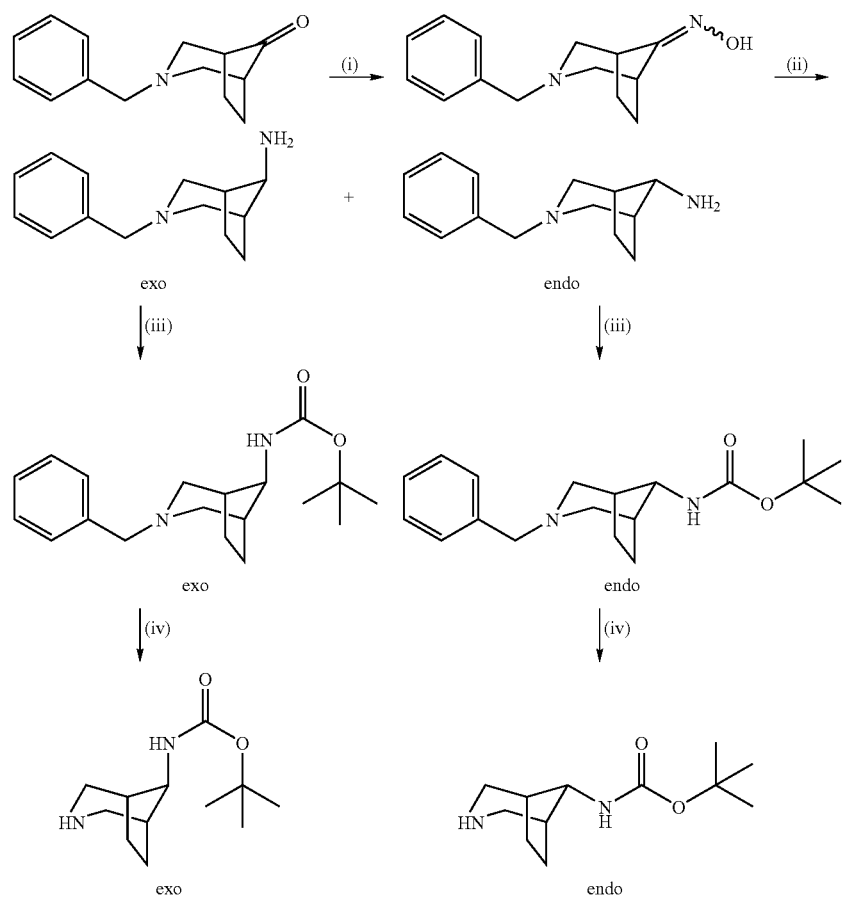

(i) NH₂OH×HCl;
(ii) Na/n-pentanol;
(iii) Boc₂O;
(iv) H₂/Pd—C

If moiety (B) stands for the group of formula (4), the starting material is the 3-benzyl-3-azabicyclo[3.3.1]nonan-9-one (J. Med. Chem. 1994, 37, 2831). Following the above reaction sequence, we did not succeed at any stage to separate the exo/endo products, and at the end of the synthesis the resulting product always contained the two isomers:

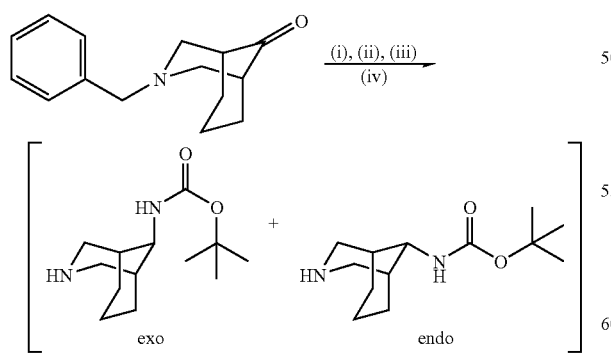

(i) NH₂OH×HCl;
(ii) Na/n-pentanol;
(iii) Boc₂O;
(iv) H₂/Pd—C;

If moiety (B) stands for the group of formula (5), the starting material is the 8-benzyl-8-azabicyclo[3.2.1]octan-3-one (J. C. S. Perkin I. 1997, 1307). From that in regioselective Grignard reaction the 8-benzyl-3-methyl-8-azabicyclo[3.2.1]octan-3-exo-ol is formed, from which, on literature analogy, the exo-acetamido derivative can be obtained in Ritter reaction (Tetrahedron Lett. 1996, 37, 1297), which, following debenzylation results the desired compound:

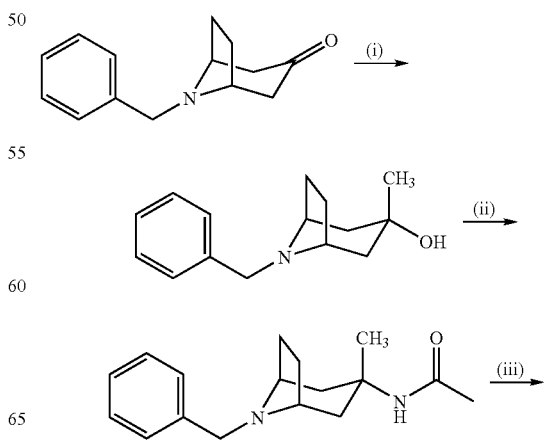

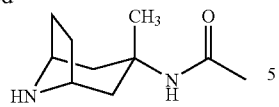

(i) MeMgBr;
(ii) MeCN, cc.H$_2$SO$_4$;
(iii) H$_2$/Pd—C;

From the resulting compounds of the general formula (V), if moiety (B) stands for the group of formula (2), (3), (4) or (5)—the Y protecting group is cleaved under acidic conditions, arriving thus to the compounds of the general formula (II). Hydrolysis is preferably carried out by trifluoroacetic acid in dichloromethane solution at a temperature between 0-30° C., or in aqueous hydrochloric acid solution or in ethanolic hydrogen chloride solution at a temperature between 25-78° C.

If moiety (B) stands for the group of formula (1), the compounds of the general formula (II) can be prepared from two different starting materials. One is the 3-hydroxy-1-aminoadamantane, (Pharm. Chem. J. (Engl. Trans.) 1990, 24, 35) from which after protecting the amino group a tert-butoxycarbonyl derivative is prepared, then treating the hydroxy group with mezyl chloride, the mezyloxy derivative is obtained. Utilising the excellent leaving capability of the leaving group, the compound is reacted with 2-amino-heterocycles—preferably in aprotic solvents or without solvent at 100-140° C.—resulting the compounds of the general formula (IV), which following treatment with trifluoroacetic acid in dichloromethane at 0-30° C., give the compounds of general formula (II):

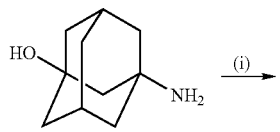

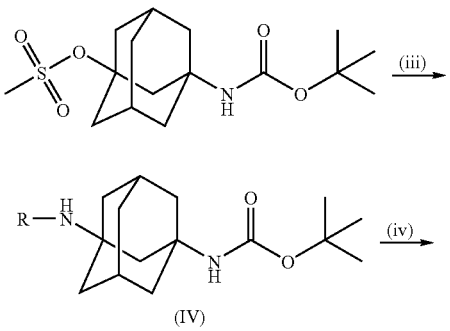

(i) Boc$_2$O;
(ii) MsCl;
(iii) R—NH$_2$;
(iv) TFA

The other starting material is the 1,3-diaminoadamantane (Ber. 1941, 74, 1769), which after acylation, alkylation or by Schiff base formation and reduction gives the compounds of general formula (II):

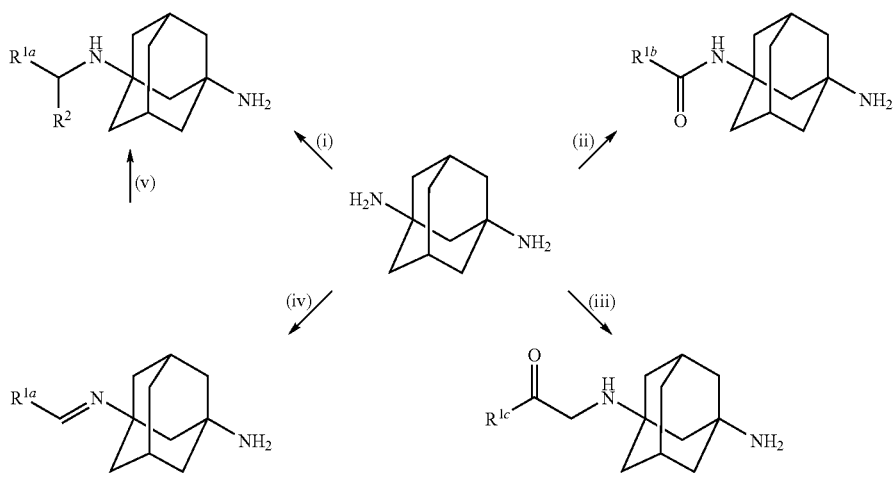

(i) R$^{1a}$R$^2$OTs;
(ii) R$^{1b}$COCl;
(iii) RCOCH$_2$Br;
(iv) R$^{1a}$CHO;
(v) NaBH$_4$;

The chloroacetyl compounds of the general formula (III)—wherein Z stands for the group of formulae (A), (B), (C), (D) or (E)—are prepared in a four-step synthesis (Scheme 3).

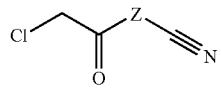

(III)

The starting compounds are the N-containing pentacyclic carboxylic acids with the nitrogen protected with tert-butoxycarbonyl group—compounds of the general formula (VI)

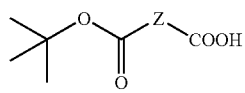

(VI)

wherein the meaning of Z is as defined above. (2S)-1-(tert-butoxycarbonyl)proline (Z=moiety (C)) and (4R)-3-(tert-butoxycarbonyl)-1,3-thiazolidine-4-carboxylic acid (Z=moiety (D)) can be purchased, (2S)-1-(tert-butoxycarbonyl)-4,4-difluoroproline (Z=moiety (A)), (2S,4S)-1-(tert-butoxycarbonyl)-4-fluoroproline (Z=moiety (B)) and (4S)-3-(tert-butoxycarbonyl)-1,3-oxazolidine-4-carboxylic acid (Z=moiety (E)) can be prepared (Tetrahedron Lett. 1998, 39, 1169 and Tetrahedron 1994, 50, 13493).

In the first step a mixed anhydride is prepared with pivaloyl or ethoxycarbonyl chloride, then the carbamoyl derivatives of the general formula (VII)

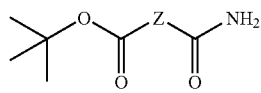

(VII)

wherein the meaning of Z is the same as defined above—are formed with aqueous ammonia. The reaction is preferably carried out in a halogenated solvent (CHCl$_3$, CH$_2$Cl$_2$) at 15° C.

In the second step the tert-butoxycarbonyl group is cleaved by ethanolic hydrogen chloride solution. Hydrolysis takes place at 0-25° C. and the hydrochlorides of the carboxamides of the general formula (VIII)

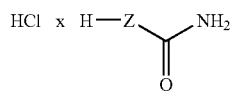

(VIII)

wherein the meaning of Z is the same as defined above—are obtained.

The resulting pentacyclic saturated carboxamides of the general formula (VIII) are in the third step acylated with chloroacetyl chloride, preferably at 0° C. in a halogenated solvent (CHCl$_3$, CH$_2$Cl$_2$) to obtain the chloroacetylcarboxamide derivatives of the general formula (IX)

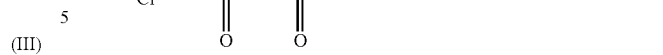

(IX)

wherein the meaning of Z is the same as defined above.

In the fourth step the chloroacetylcarboxamide derivatives of the general formula (IX)—wherein the meaning of Z is as defined above—are dehydrated to yield the chloroacetylcyano derivatives of the general formula (III). Dehydratation is generally carried out with phosphoryl chloride in dichloromethane at reflux temperature, or with oxalyl chloride in the presence of DMF, at a temperature lower than 0° C.

Scheme 1.

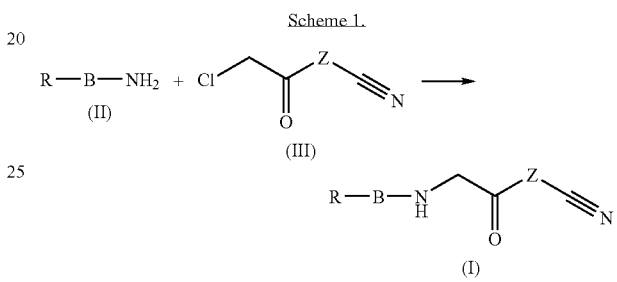

Scheme 2.

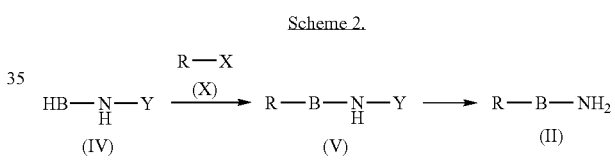

Scheme 3.

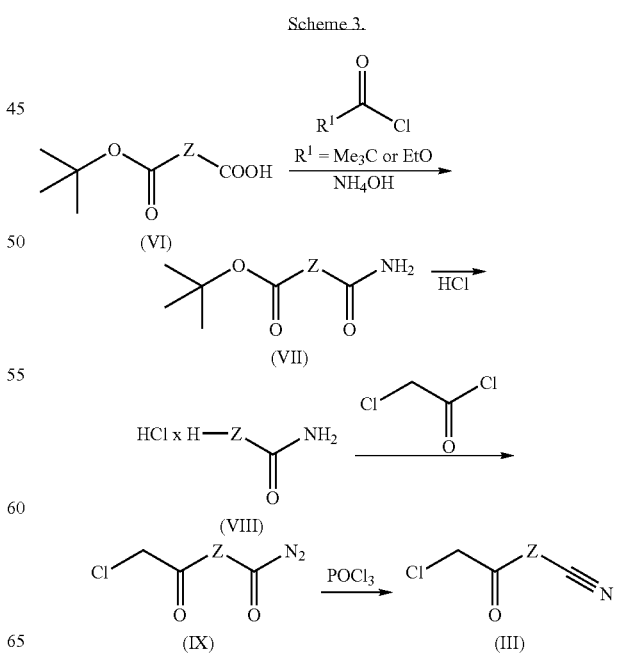

Biological Investigations

DPP-IV enzyme inhibitory activties of the compounds with the general formula (I) were determined by the following method:

Applied Conditions of the Assay:

| | |
|---|---|
| DPP-IV. source: | solubilized crude extractum from CaCo/Tc-7 cells content: 0.8-1 µg/assay |
| Substrate: | H-Gly-Pro-AMC (Bachem) |
| Reaction: | 1 hour preincubation with samples at 37° C., 30 mm reaction time at 37° C. |
| Stop solution: | 1 M Na-acetate buffer (pH = 4.2) |
| Reaction mixture: | 10 µl enzyme solution |
| | 10 µl test compound or assay buffer |
| | 55 µl assay buffer |
| | 25 µl substrate |
| | 300 µl stop solution |
| Measurement: | spectrofluorometric determination by Tecan plate reader (Ex: 360 nm Em: 465 nm) |

The reaction of the DPP-IV enzyme and the H-Gly-Pro-AMC substrate is recorded by the liberation of AMC (7-amino-4-methylcoumarin) at 37° C. in 100 mM Tris-HCl, pH=7.5 (assay buffer). Standard curve of AMC is linear up to 31.25 µM concentration, therefore we used the relative fluorescence unit (RFU) of the AMC formed. It is detected using 360 nm excitation and 465 emmission filters (integration time 30 µs, Gain 25, No. of Flashes 50) by Tecan Spectrofluor Plus plate reader. Under these conditions enzyme reaction is linear for at least 30 min, and the enzyme dependence is linear up to 2.5 µg protein (up to 700 RFU). Using 1-0.8 µg of extracted protein $K_m$ for H-Gly-Pro-AMC is 50 µM. Higher than 500 µM substrate concentration caused fluorescent detection problems (inner filter effect) that can be solved by dilution of the samples.

The assay is designed to detect as efficiently as possible the active inhibitors using a 60 min preincubation time at 37° C. The assay is conducted by adding 0.8-1 µg protein extract in 10 µl enzyme sulution (using assay buffer: 100 mM Tris-HCl, pH=7.5) to the wells containing the test compounds in 10 µl volume and the 55 µl assay buffer (65 µl assay buffer in the case of controls). After the preincubation period, the reaction is started by the addition of 25 µlmM H-Gly-Pro-AMC substrate solution (250 µM final concentration). The final test volume is 100 µl and the test solution contains 1% DMSO coming from the test compounds solution. Reaction time is 30 min at 37° C., and the reaction is stopped by adding 300 µl 1M Na-acetate buffer, pH=4.2. The fluorescence (RFU) of AMC formed is detected using 360 nm excitation and 465 emission filters in Tecan spectrofluor Plus plate reader (30 µs integration time, Gain 25 No. of Flashes 50). Inhibition % are calculated using the RFU of control and RFU of blank.

The $IC_{50}$ values are characteristic for the enzyme inhibitory effect of the compounds of the general formula (I) according to the invention. The compounds of the general formula (I) exhibit low $IC_{50}$ values, generally below 100 nM. For example the endproduct of (2S)-1-[N-(3-pyrimidin-2-yl-3-azabicyclo[3.2.1]oct-8-yl)glycyl]pyrrolidine-2-carbonitrile (Example 40) shows $IC_{50}$ value of 30 nM, endproduct of (4S)-3-{N-[3-(pyrimidin-2-ylamino)-1-adamantyl]glycyl}-1,3-oxazolidine-4-carbonitrile (Example 9) shows $IC_{50}$ value of 21 nM and endproduct of (2S)-1-(N-{3-[(4-cyanobenzyl)amino]-1-adamantyl}glycyl)-4,4-difluoropyrrolidine-2-carbonitrile (Example 27) shows $IC_{50}$ value of 16 nM. Their duration of action and their activity are therapeutically favourable.

The compounds of the general formula (I) and their solvates, isomers, salts and solvates of their salts can be formulated to orally or parenterally applicable pharmaceutical compositions by methods known per se, by mixing them with one or more pharmaceutically accepted support material or diluent and can be administered as a unitary dosage form.

As a consequence of their higher water solubility compared to the starting or basic compounds, pharmaceutically acceptable salts are particularly suitable for medical applications. These salts have to have a pharmaceutically acceptable anion or cation. Suitable pharmaceutically acceptable acid addition salts of the compounds according to the invention are salts of inorganic acids such as hydrochloric acid, hydrobromic acid, phosphoric acid, metaphosphoric acid, nitric acid and sulfuric acid, and also organic acids, e.g. acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts having a pharmaceutically unacceptable anion, for example trifluoroacetate, are likewise encompassed by the scope of the invention as useful intermediates for the preparation or purification of pharmaceutically acceptable salts and/or for use in nontherapeutic, for example in vitro, applications.

As used herein, the following definitions apply:

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

"Pharmaceutically acceptable salts" means either an acid addition salt or a basic addition salt which is compatible with the treatment of patients for the intended use.

"Pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents and which in comparison to their free base forms, generally demonstrate higher melting points.

"Pharmaceutically acceptable basic addition salts" means non-toxic organic or inorganic basic addition salts of the compounds of Formula (I) or any of its intermediates. Examples are alkali metal or alkaline-earth metal hydroxides such as sodium, potassium, calcium, magnesium or barium hydroxides; ammonia, and aliphatic, alicyclic, or aromatic organic amines such as methylamine, trimethylamine and picoline. The selection criteria for the appropriate salt will be known to one skilled in the art.

"Disease or disorder associated with DPP-IV enzyme activity" means a disease, disorder or condition which includes, but is not limited to, non-insulin dependent diabetes mellitus (NIDDM), diabetes, obesity, hyperlipidemia, dermatological or mucous membrane disorders, psoriasis, intestinal distress, constipation, autoimmune disorders such as encephalomyelitis, complement metiated disorders such as glomerulonephritis, lipodystrohy and tissue damage, psychosomatic, depressive and neuropsychiatric disease such as anxiety, depression, insomnia, schizophrenia, epilepsy, spasm and chronic pain, HIV infection, allergies, inflammation, arthritis, transplant rejection, high blood pressure, congestive heart failure, tumors and stress-induced abortions.

The compound(s) of the formula (I) can also be administered in combination with further-active ingredients.

The amount of a compound of formula I which is required in order to achieve the desired biological effect is dependent upon a series of factors, for example the specific compound selected, the intended use, the mode of administration and the clinical condition of the patient. The daily dose is generally in the range from 0.3 mg to 100 mg (typically from 3 mg and 50 mg) per day per kilogram of bodyweight, for example 3-10 mg/kg/day. An intravenous dose may, for example, be in the range from 0.3 mg to 1.0 mg/kg and may advantageously be administered as an infusion of from 10 ng to 100 ng per kilogram per minute. Suitable infusion solutions for these purposes may, for example, contain from 0.1 ng to 10 mg, typically from 1 ng to 10 mg, per milliliter. Individual doses may contain, for example, from 1 mg to 10 g of the active ingredient. Ampoules for injections may therefore contain, for example, from 1 mg to 100 mg, and single dose formulations which can be administered orally, for example tablets or capsules, may contain, for example, from 1.0 to 1000 mg, typically from 10 to 600 mg. The compounds of formula I may be used for therapy of the abovementioned conditions as the compounds themselves, although they are preferably in the form of a pharmaceutical composition with an acceptable carrier. The carrier of course has to be acceptable, in the sense that it is compatible with the other constituents of the composition and is not damaging to the health of the patient. The support may be a solid or a liquid or both and is preferably formulated with the compound as a single dose, for example as a tablet, which may contain from 0.05 to 95% by weight of the active ingredient. Further pharmaceutically active substances may likewise be present, including further compounds of formula I. The pharmaceutical compositions according to the invention may be produced by one of the known pharmaceutical methods which consist essentially of mixing the ingredients with pharmacologically acceptable carriers and/or excipients.

Pharmaceutical compositions according to the invention are those which are suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the type of the compound of formula I used in each case. Coated formulations and coated slow-release formulations are also encompassed by the scope of the invention. Preference is given to acid- and gastric fluid-resistant formulations. Suitable gastric fluid-resistant coatings include cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units, for example capsules, cachets, lozenges or tablets, each of which contains a certain amount of the compound of formula I; as powder or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. In general, the compositions are prepared by uniform and homogeneous mixing of the active ingredient with a liquid and/or finely divided solid carrier, after which the product is shaped if necessary. For example, a tablet can be produced by compressing or shaping a powder or granules of the compound, optionally with one or more additional ingredients. Compressed tablets can be prepared by tableting the compound in free-flowing form, for example a powder or granules, optionally mixed with a binder, lubricant, inert diluent and/or one (or more) surfactants/dispersants in a suitable machine. Shaped tablets can be prepared by shaping the pulverulent compound moistened with an inert liquid diluent in a suitable machine.

Pharmaceutical compositions which are suitable for peroral (sublingual) administration include lozenges which contain the compound of formula I with a flavoring, customarily sucrose, and gum arabic or tragacanth, and pastilles which include the compound in an inert base such as gelatin and glycerol or sucrose and gum arabic.

Suitable pharmaceutical compositions for parenteral administration include preferably sterile aqueous preparations of a compound of formula I which are preferably isotonic with the blood of the intended recipient. These preparations are preferably administered intravenously, although the administration may also be subcutaneous, intramuscular or intradermal as an injection. These preparations can preferably be produced by mixing the compound with water and making the solution obtained sterile and isotonic with the blood.

The injectable compositions according to the invention generally contain from 0.1 to 5% by weight of the active compound.

Suitable pharmaceutical compositions for rectal administration are preferably in the form of single dose suppositories. These can be prepared by mixing a compound of formula I with one or more conventional solid carriers, for example cocoa butter, and shaping the resulting mixture.

Suitable pharmaceutical compositions for topical use on the skin are preferably in the form of an ointment, cream, lotion, paste, spray, aerosol or oil. Useful carriers include petroleum jelly, lanolin, polyethylene glycols, alcohols and combinations of two or more of these substances. The active ingredient is generally present in a concentration of from 0.1 to 15% by weight of the composition, preferably from 0.5 to 2%.

Transdermal administration is also possible. Suitable pharmaceutical compositions for transdermal applications may be in the form of single plasters which are suitable for long-term close contact with the epidermis of the patient. Such plasters advantageously contain the active ingredient in an optionally buffered aqueous solution, dissolved and/or dispersed in an adhesive or dispersed in a polymer. A suitable active ingredient concentration is from approx. 1% to 35%, preferably from approx. 3 to 15%. A particular means of releasing the active ingredient is by electrotransport or iontophoresis, as described, for example, in Pharmaceutical Research, 2(6): 318 (1986).

As an example, a unitary dosage form for a compound according to the invention, in the form of a tablet, can comprise the following ingredients:

| | |
|---|---|
| A compound of the general formula (I) | 50.0 mg |
| Mannitol | 223.75 mg |
| Croscarmellose sodium | 6.0 mg |
| Maize starch | 30.0 mg |
| Hydroxypropyl methylcellulose | 2.25 mg |
| Magnesium stearate | 3.0 mg |

The daily dose of the compounds of the general formula (I) depends on several factors, thus on the nature and severeness of the disease of the patient, on the mode of application and on the compound itself.

The following examples illustrate the preparation of the compounds of the general formula (I) but not at all limit the scope of the invention.

EXAMPLE 1

(2S)-4,4-difluoro-1-{N-[3-(pyrimidin-2-ylamino)-1-adamantyl]glycyl}pyrrolidine-2-carbonitrile dihydrochloride monohydrate In general formula (I) R stands for pyrimidin-2-yl group, B stands for the group of formula (1), Z stands for the group of formula (A).

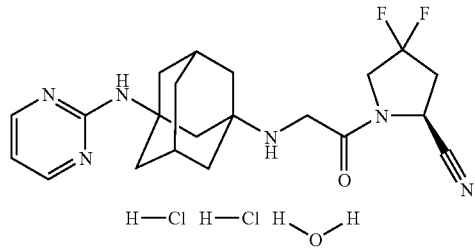

a.) tert-Butyl[3-(pyrimidin-2-ylamino)-1-adamantyl]carbamate

In general formula (V) the meaning of R and B are as defined above, Y represents tert-butoxycarbonyl group.

(i) tert-Butyl(3-hydroxy-1-adamantyl)carbamate 2.51 g (15 mmole) of 3-hydroxy-1-aminoadamantane (Pharm. Chem. J. (Engl. Trans.) 1990, 24, 35) are dissolved in the mixture of 15 ml of dioxane, 15 ml of water and 15 ml of 1N sodium hydroxide solution, then under cooling and stirring 4.91 g (22.5 mmole) of di-tert-butyl dicarbonate are added. The mixture is stirred at room temperature for 16 hours, the solution is evaporated, and the residue is dissolved in the mixture of 50 ml of ethyl acetate and 50 ml of water. Following extraction and separation of the phases, the organic phase is dried over sodium sulphate. After evaporation the white crystalline residue is treated with n-hexane, to obtain 2.61 g (65%) of product. M.p.: 131-132° C. $^1$H-NMR.: (DMSO-$d_6$): 1.36 (s, 9H), 1.41 (s, 2H), 1.48 (d, 4H), 1.70 (d, 6H), 2.10 (bs, 2H), 4.43 (s, 1H), 6.41 (s, 1H).

(ii) 3-[(tert-Butoxycarbonyl)amino]-1-adamantyl methanesulphonate 5.6 g (21 mmole) of tert-butyl(3-hydroxy-1-adamantyl) carbamate are dissolved in 80 ml of dichloromethane, 4.4 ml (31.5 mmole) of triethylamine are added to it. The mixture is cooled to 0° C. and 1.82 ml (23.5 mmole) of methanesulphonyl chloride is added to it dropwise. The reaction mixture is stirred at that temperature for 45 minutes, then washed consecutively with water and saturated sodium hydrogen carbonate solution. The organic phase is dried over sodium sulphate, evaporated, the residue is purified by column chromatography (n-hexane—ethyl acetate—chloroform 2:1:1) and crystallised from n-hexane, to obtain 2.9 g (40%) of product: Mp.: 100-102° C. $^1$H-NMR (DMSO-$d_6$): 1.37 (s, 9H), 1.48 (s, 2H), 1.77 (q, 4H), 2.05 (t, 4H), 2.17 (d, 2H), 3.10 (s, 3H), 6.66 (s, 1H).

(iii) tert-Butyl[3-(pyrimidin-2-ylamino)-1-adamantyl]carbamate

The mixture of 1.04 g (3 mmole) of 3-[(tert-butoxycarbonyl)amino]-1-adamantyl methanesulphonate and 1.0 g (10.5 mmole) 2-aminopyrimidine are melted at 140° C. After 15 minutes of stirring the melt is cooled down and purified by column chromatography (n-hexane—ethyl acetate—chloroform 2:1: 1). The product is white crystalline material, 0.7 g (68%). Mp.: 163-165° C. $^1$H-NMR (DMSO-$d_6$): 1.36 (s, 9H), 1.52 (s, 2H), 1.71 (d, 2H), 1.86 (d, 4H), 2.07 (m, 4H), 2.25 (m, 2H), 6.38 (s, 1H), 6.49 (t, 3H), 6.58 (s, 1H), 8.22 (d, 2H).

b.) N-pyrimidin-2-yladamantane-1,3-diamine dihydrochloride

In general formula (II) the meaning of R and B is as defined above.

700 mg (2 mmole) of tert-butyl[3-(pyrimidin-2-ylamino)-1-adamantyl]carbamate are dissolved in 25 ml of 20% ethanolic hydrogen chloride solution. The mixture is stirred at room temperature for 24 hours, evaporated to dryness; the residue is treated with acetone to obtain white crystalline material: 453 mg (68%). M.p.: 301-304° C. $^1$H-NMR (DMSO-$d_6$): 1.56 (q, 2H), 1.78 (s, 4H), 2.00 (q, 4H), 2.24 (s, 4H), 6.78 (t, 1H), 8.21 (br, 3H), 7.85 (br, 1H), 8.46 (d, 2H).

c.) tert-Butyl(2S)-2-(aminocarbonyl)-4,4-difluoropyrrolidine-1-carboxylate

In general formula (VII) Z stands for the group of formula (A)

5.7 g (22.7 mmole) of (2S)-1-(tert-butoxycarbonyl)-4,4-difluoroproline (Tetrahedron Lett. 1998, 39, 1169) are dissolved in 57 ml of dichloromethane and to the solution 3.8 ml (27.2 mmole) of triethylamine are added. To the resulting mixture at −15° C. 3 ml (25 mmole) of pivaloyl chloride is added, the reaction mixture is stirred at that temperature for 1 hour, then 7 ml of 25% aqueous ammonia solution is added to it dropwise and stirring is continued for an additional hour. The reaction mixture is washed with water, with 1 N sodium hydroxide solution, and with water, dried over sodium sulphate and evaporated. The product is crystallised from diethyl ether to obtain 3.94 g (69%) of the title product. M.p.: 136-138° C. $^1$H-NMR (CDCl$_3$): 1.48 (s, 9H); 2.3-2.9 (m, 3-CH$_2$), 3.69 (br, minor)+3.86 (m, major)(5-CH$_2$), 4.53 (br, 2-CH), 6.0 (br, major)+6.81 (br, minor)(NH$_2$).

d.) (2S)-4,4-Difluoroprolinamide hydrochloride

In general formula (VIII) Z stands for the group of formula (A).

3.93 g (15.7 mmole) of tert-butyl(2S)-2-(aminocarbonyl)-4,4-difluoro-pyrrolidine-1-carboxylate are dissolved in 75 ml of 25% ethanolic hydrogen chloride solution and stirred at room temperature for 4 hours. To the resulting suspension 150 ml of diethyl ether is added and the white crystalline material is filtered off, to obtain 2.55 g (87%) title product. M.p.: 232-233° C. $^1$H-NMR (DMSO-d$_6$): 2.43-2.51 (m, minor)+2.81-3.05 (m, major)(3-CH$_2$), 3.71 (t, 2H, 5-CH$_2$), 4.46 (t, 1H, 2-CH), 7.81 (s, 1H,)+8.12 (s, 1H)(NH$_2$), 10.12 (br, 2H, NH$_2^+$).

e.) (2S)-1-(Chloroacetyl)-4,4-difluoroprolinamide

In general formula (IX) Z stands for the group of formula (A).

2.54 g (13.6 mmole) of (2S)-4,4-difluoroprolinamide hydrochloride are suspended in 25 ml of dichloromethane, 4.1 ml (29.3 mmole) of triethylamine is added to it, and to the mixture, below −10° C., the solution of 1.2 ml (15 mmole) of chloroacetyl chloride in 20 ml dichloromethane are added dropwise. After 1 hour of stirring the suspension is poured onto 450 ml of ethyl acetate, the precipitated triethylamine hydrochloride is filtered off. The filtrate is evaporated and purified by chromatography using chloroform-methanol 4:1 mixture as eluent. 3.0 g (97%) colourless oil is obtained, which is crystallised after a few days of standing. M.p.: 118-121° C. $^1$H-NMR (DMSO-d$_6$): 2.34-2.52 (m, 1H)+2.66-2.83 (m, 1H)(3-CH$_2$), 4.07-4.29 (m, 2H, 5-CH$_2$), 4.40 (qv, 2H, CH$_2$Cl), 4.71 (m, 1H, 2-CH), 7.17 (br, 1H)+7.42 (d, 1H) (NH$_2$).

f.) (2S)-1-(Chloroacetyl)-4,4-difluoropyrrolidine-2-carbonitrile

In general formula (III) Z stands for the group of formula (A).

10.4 g (40 mmole) of (2S)-1-(Chloroacetyl)-4,4-difluoroprolinamide are dissolved in 230 ml of dichloromethane and to the solution 13 ml (140 mmole) of phosphorus oxychloride are added. The mixture is heated under reflux for 24 hours. In the course of the heating the solution turns into yellow and a small amount of dark resin also precipitates. The solution is transferred into a larger container, 50 g of potassium carbonate is added to it and stirred for 1 hour. The solid salts are filtered off; the filtrate is evaporated to obtain yellow oil, which crystallises from n-hexane. The crude product is treated with 70 ml of diethyl ether to obtain 6.0 g (56%) white crystalline material. M.p.: 86-87° C. $^1$H-NMR (CDCl$_3$): 2.76-2.98 (m, 2H, 3-CH$_2$), 3.92-4.26 (m, 2H, 5-CH$_2$), 4.46 (q, 2H, CH$_2$Cl), 5.11 (m, 1H, 2-CH).

g.) (2S)-4,4-difluoro-1-{N-[3-(pyrimidin-2-ylamino)-1-adamantyl]glycyl}pyrrolidine-2-carbonitrile dihydrochloride monohydrate 424 mg (1.3 mmole) of N-pyrimidin-2-yladamantane-1,3-diamine dihydrochloride are suspended in 10 ml of dichloromethane and extracted with 10 ml of saturated sodium carbonate solution. The organic phase is dried over sodium sulphate and evaporated. The residue is dissolved in 10 ml of acetonitrile, to the solution 229 mg (1.1 mmole) of (2S)-1-(chloroacetyl)-4,4-difluoropyrrolidine-2-carbonitrile and 0.42 ml (3 mmol) of triethylamine are added. The mixture is stirred at room temperature for 40 hours, evaporated. The residue is dissolved in 30 ml of dichloromethane, washed with water, dried over sodium sulpfate and evaporated. The yellowish-coloured residue is purified by column chromatography (chloroform-methanol 6:1), the product is obtained in the form of an oil, which gives dihydrochloride salt with ethereal hydrochloric acid: 160 mg (29%), m.p.: 209-212° C. $^1$H-NMR (DMSO-d$_6$): 1.50 (d, 1H), 1.60 (d, 1H), 1.88 (m, 6H), 2.11 (m, 2H), 2.31 (s, 4H), 2.84-2.93 (m, 2H), 4.00 (m, 1H), 4.01-4.17 (m, 2H), 4.32 (m, 1H), 5.18 (dd, 1H), 6.72 (t, 1H), 7.61 (b, 1H), 8.40 (d, 2H), 9.10 (s, 2H).

EXAMPLE 2

(2S)-4,4-difluoro-1-(N-{3-[(3-nitrobenzyl)amino]-1-adamantyl}glycyl)pyrrolidine-2-carbonitrile trihydrochloride In general formula (I) R stands for 3-nitrobenzyl group, B stands for the group of formula (1), Z stands for the group of formula (A).

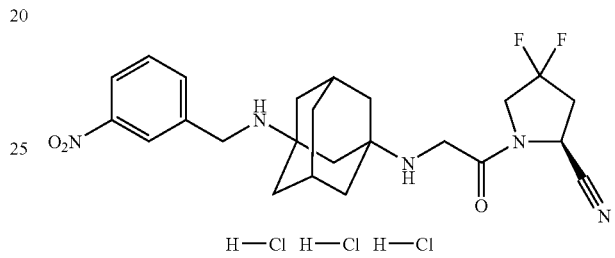

a.) N-(3-Nitrobenzyl)adamantane-1,3-diamine

In general formula (II) the meaning of R and B is as defined above.

287 mg (1.2 mmole) of 1,3-diamino-adamantane dihydrochloride (Chem. Ber. 1941, 1769) are suspended in 30 ml of dichloromethane and extracted with 30 ml of saturated sodium carbonate solution. The organic phase is dried over sodium sulphate and evaporated. The residue is dissolved in 30 ml of toluene, to the solution 90 mg (0.6 mmole) of 3-nitrobenzaldehyde and 10 mg p-toluenesulfonic acid monohydrate are added. The mixture is reluxed for 2 hours, and then evaporated, the residue is dissolved in 30 ml methanol, to the solution 114 mg (3 mmole) sodium borohydride are added. After 16 hours of stirring at room temperature solution is evaporated, the residue is dissolved in dichloromethane and washes with water. The organic layer was dried over sodium sulphate, evaporated and purified by column chromatography (chloroform-methanol-25% aqueous ammonia solution 9:1:0.05). The product is obtained in the form of thick oil, which is crystallized after standing: 93 mg (26%). $^1$H-NMR (DMSO-d$_6$): 1.40 (m, 10H), 1.46 (s, 2H), 2.08 (s, 2H), 3.80 (s, 2H), 7.56 (t, 1H), 7.78 (d, 1H), 8.05 (d, 1H), 8.23 (s, 1H).

b.) (2S)-4,4-difluoro-1-(N-{3-[(3-nitrobenzyl)amino]-1-adamantyl}glycyl)pyrrolidine-2-carbonitrile trihydrochloride 90 mg (0.3 mmole) of N-(3-nitrobenzyl)adamantane-1,3-diamine and 50 mg (0.24 mmole) of (2S)-1-(chloroacetyl)-4,4-difluoropyrrolidine-2-carbonitrile are dissolved in acetonitrile, to the solution 300 mg (0.75 mmole) of polymer bound 2-tert-butylimino-2-diethylamino-1,3-dimethyl-perhydro-1,3,2-diazaphosphorine (PBEMP) are added. The mixture is sirred at 70° C. for 4 hours, then at room temperature for 20 hours. The scavanger resin is fitered off and the filtrate is evapotared, the residue is purified by column chromatography (chloroform-methanol 6:1). After acidification of the formed oil with ethereal hydrochloride acide the title compound is obtained: 41 mg (29%), m.p.: 226-229° C. $^1$H-NMR (DMSO-$d_6$): 1.57 (s, 2H), 1.95 (d, 8H), 2.45 (d, 4H), 2.91 (m, 2H), 4.14 (m, 2H), 4.33 (m, 4H), 5.21 (m, 1H), 7.74 (t, 1H), 8.15 (t, 1H), 8.27 (dd, 1H), 8.58 (s, 1H), 9.41 (b, 2H), 9.77 (b, 2H).

EXAMPLE 3

N-(3-{[2-(2-cyano-(2S)-4,4-difluoropyrrolidin-1-yl)-2-oxoethyl]amino}-1-adamantyl)-4-methoxybenzamide dihydrochloride monohydrate In general formula (I) R stands for 4-methoxybenzoyl group, B stands for the group of formula (1), Z stands for the group of formula (A).

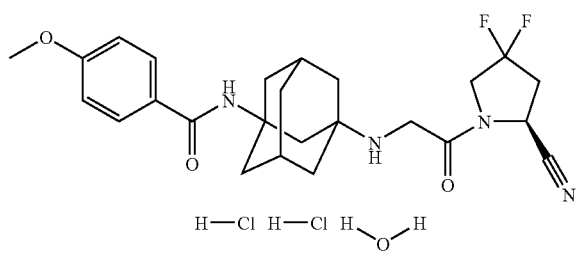

a.) N-(3-Amino-1-adamantyl)-4-methoxybenzamide

In general formula (II) the meaning of R and B is as defined above.

Free base is prepared from 487 mg (2 mmole) of 1,3-diamino-adamantane dihydrochloride, as described in Example 2/a.). It is dissolved in 20 ml of dichlorometane, to the solution 253 mg (2.1 mmole) polimer-bound dietilamine (PS-DIEA) are added, and to the mixture at 0° C. the solution of 119 mg (0.7 mmole) of p-anisoyl chloride in 20 ml of dichloromethane are added dropwise. After stirring 24 hours the solid materials are filtered off and the filtrate is evaporated. The residue is purified by column chromatography (chloroform-methanol-25% aqueous ammonia solution 9:1: 0.1): 132 mg (63%) $^1$H-NMR (DMSO-$d_6$): 1.41 (m, 6H), 1.89 (d, 6H), 2.11 (s, 2H), 3.80 (s, 3H), 6.96 (d, 2H), 7.47 (s, 1H), 7.76 (d, 2H).

b.) N-(3-{[2-(2-cyano-(2S)-4,4-difluoropyrrolidin-1-yl)-2-oxoethyl]amino}-1-adamantyl)-4-methoxybenzamide dihydrochloride monohydrate 132 mg (0.45 mmole) of N-(3-Amino-1-adamantyl)-4-methoxybenzamide are reacted with 87 mg (0.42 mmole) of (2S)-1-(chloroacetyl)-4,4-difluoro-pyrrolidine-2-carbonitrile in the presence 340 mg (1.32 mmole) PS-DIEA in 25 ml acetonitrile, as described in Example 2/b.). After work-up and chromatographic purification (chloroform-methanol-25% aqueous ammonia solution 9:1:0.1) and acidification ethereal hydrochloride acide the title compound is obtained: 90 mg (46%). M.p.: 160-161° C. $^1$H-NMR (DMSO-$d_6$): 1.60 (dd, 2H), 1.85 (m, 6H), 2.14 (m, 2H), 2.30 (m, 2H), 2.38 (m, 2H), 2.87 (m, 2H), 3.79 (s, 3H), 4.17 (m, 2H), 4.26 (m, 1H), 4.47 (m, 1H), 5.21 (m, 1H), 6.95 (d, 2H), 7.71 (s, 1H), 7.77 (d, 2H), 9.41 (b, 2H), 9.02 (b, 2H).

EXAMPLE 4

(2S)-4,4-difluoro-1-[N-(3-pyrimidin-2-yl-3-azabicyclo[3.2.1]oct-8-yl)exo-aminoacetyl]pyrrolidine-2-carbonitrile In general formula (I) R stands for pyrimidin-2-yl group, B stands for the group of formula (3), Z stands for the group of formula (A).

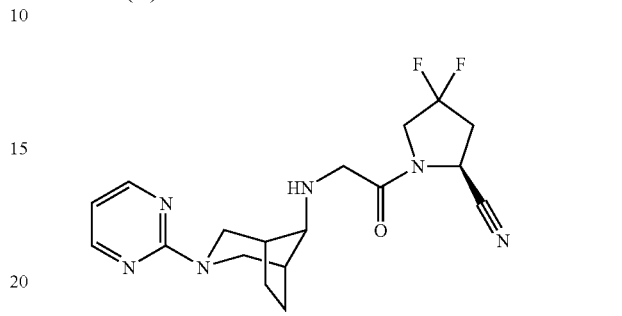

a.) tert-Butyl(3-pyrimidin-2-yl-3-azabicyclo[3.2.1]oct-8-yl)-exo-carbamate

In general formula (V) the meaning of R and B, are as defined above, Y represents tert-butoxycarbonyl group.

(i) 3-Benzyl-3-azabicyclo[3.2.1]octan-8-one oxime

The mixture of 19 g (88 mmole) of 3-benzyl-3-azabicyclo [3.2.1]octan-8-one (J. Med. Chem. 1994, 37, 2831), 200 ml of ethanol, 8.78 g (126.4 mmole) of hydroxylamine hydrochloride and 13 ml of pyridine are heated and stirred on a 100° C. oil-bath, then the mixture is evaporated. To the residue 65 ml of 2.5 N sodium hydroxide solution is added, the resulting solution is extracted with 3×120 ml of ethyl acetate. The extractum is dried over sodium sulphate and evaporated. The resulting oil is purified by column chromatography (n-hexane-ethyl acetate from 9:1 to 1:1) to obtain 11.05 g (54%) of white, crystalline material. M.p.: 92-95° C. (MH$^+$)=231.

(ii) 3-Benzyl-3-azabicyclo[3.2.1]octan-8-exo-amine and 3-benzyl-3-azabicyclo[3.2.1]octan-8-endo-amine

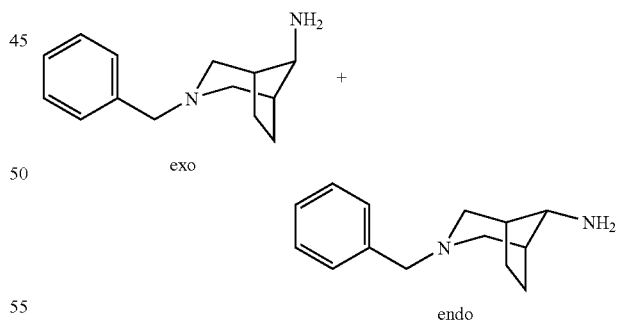

11.05 g (48 mmole) of 3-benzyl-3-azabicyclo[3.2.1]octan-8-one oxime are dissolved at room temperature in 300 ml of n-pentanol. To the boiling solution under nitrogen stream and intensive stirring, in several portions 12 g (52 mmole) of sodium metal is added in small peaces. At the end of the addition the raction mixture is heated under reflux for an additional half an hour. After cooling the mixture is poured onto 250 ml of cold water. The phases are separated; the organic phase is washed with 100 ml of cold water and extracted with 3×100 ml of 2N hydrochloric acid. Carefully, under cooling, the acidic solution is made alkaline (pH=13) with solid potassium hydroxide and the mixture is extracted with dichloromethane. The extract is dried over sodium sulphate and evaporated. The residue is purified by column chromatography (dichloromethane-methanol from 95:5 to 4:1) to obtain separately 4.52 g (44%) of the exo-isomer (m.p. 61-63° C.) and 1.07 g (10%) of the endo-isomer (m.p. 70-72° C.). (MH$^+$)=217.

(iii) tert-Butyl(3-benzyl-3-azabicyclo[3.2.1]oct-8-yl)-exo-carbamate

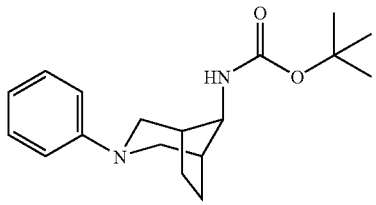

4.50 g (21 mmole) of 3-benzyl-3-azabicyclo[3.2.1]octan-8-exo-amine are dissolved in 10 ml of dichoromethane and to the solution 5.71 g (26 mmole) of di-tert-butyl dicarbonate in 10 ml of dichoromethane are added under cooling. The mixture is stirred at room temperature for 2 hours, evaporated and crystallized from n-hexane, to obtain: 5.47 g (83%). M.p.: 118-119° C. $^1$H-NMR (DMSO-d$_6$): 1.40 (s, 9H), 1.58-1.67 (m, 4H), 2.00 (s, 2H), 2.28 (dd, 2H), 2.45 (d, 2H), 3.37 (d, 1H), 3.46 (d, 2H), 6,83 (s, 1H), 7.19-7.30 (m, 5H). (MH$^+$)=317.

(iv) tert-Butyl 3-azabicyclo[3.2.1]oct-8-yl-exo-carbamate 5.4 g (17 mmole) of tert-Butyl(3-benzyl-3-azabicyclo[3.2.1]oct-8-yl)-exo-carbamate are dissolved in 50 ml of methanol, to the solution 1.8 g of 10% palladium on charcoal are added and the mixture is hydrogenated under small pressure (3-5 atm). The catalyst is filtered off, the filtrate is evaporated, the residue is crystallised from the mixture of diethyl ether and n-hexane to obtain 3.85 g (96%) of product. M.p.: 93-94° C. (MH$^+$)=227.

(v) tert-Butyl(3-pyrimidin-2-yl-3-azabicyclo[3.2.1]oct-8-yl)-exo-carbamate

The mixture of 2.32 g (10 mmole) of tert-butyl 3-azabicyclo[3.2.1]oct-8-yl-exo-carbamate, 1.15 g (10 mmole) of 2-chloropyrimidine, 1.8 ml (12 mmole) of DBU and 20 ml of acetonitrile are stirred at room temperature for 24 hours. The reaction mixture is evaporated, after addition of 20 ml of water to the residue, it is extracted with 3×10 ml of dichloromethane. The extract is dried over sodium sulphate and evaporated. The residue is purified by chromatography on silica gel with dichloromethane eluent, to obtain 1.91 g (61%) of white, crystalline product. M.p.: 145-146° C. (MH$^+$)=305.

b.) 3-Pyrimidin-2-yl-3-azabicyclo[3.2.1]octan-8-exo-amine

In general formula (II) the meaning of R and B are as defined above

To the solution of 2.1 g (6.9 mmole) of tert-butyl(3-pyrimidin-2-yl-3-azabicyclo[3.2.1]oct-8-yl)-exo-carbamate in 35 ml of dichloromethane, 16.1 ml of trifluoroacetic acid are added. The reaction mixture is stirred at room temperature, then evaporated. The pH is adjusted pH=9 with saturated sodium carbonate solution, under cooling; the mixture is then extracted with dichloromethane. The organic layer is dried over sodium-sulphate and evaporated. The residue is suspended in n-hexane, after cooling the solid material is filtered off, dried, to obtain 0.63 g (45%) of white crystals. M.p.: 105-107° C. (MH$^+$)=205.

c.) (2S)-4,4-difluoro-1-[N-(3-pyrimidin-2-yl-3-azabicyclo[3.2.1]oct-8-yl)exo-aminoacetyl]pyrrolidine-2-carbonitrile 204 mg (1.0 mmole) of 3-pyrimidin-2-yl-3-azabicyclo[3.2.1]octan-8-exo-amine and 208 mg (1 mmole) of (2S)-1-(chloroacetyl)-4,4-difluoropyrrolidine-2-carbonitrile and 0.25 ml (1.8 mmole) of triethylamine are reacted in acetonitrile as described in Example 1/g). After purification by column chromatography (dichloromethane-methanol 9:1) and treatment with n-hexane, white crystalline product is obtained: 200 mg (53%). M.p.: 50-52° C. $^1$H-NMR (DMSO-d$_6$): 1.44 (td, 2H), 1.67 (m, 2H), 2.18 (s, 2H), 2.42 (br, 1H), 2.81 (m 3H), 3.31 (m, 2H), 3.47 (m, 2H), 3.98 (m, 3H), 4.18 (m, 1H), 5.08 (dd, 1H), 6.56 (t, 1H), 8.32 (d, 2H). (MH$^+$)=377.

EXAMPLE 5

(2S)-4,4-difluoro-1-[N-(3-pyrimidin-2-yl-3-azabicyclo[3.2.1]oct-8-yl)endo-aminoacetyl]pyrrolidine-2-carbonitrile dihydrochloride In general formula (I) R stands for pyrimidin-2-yl group, B stands for the group of formula (2), Z stands for the group of formula (A).

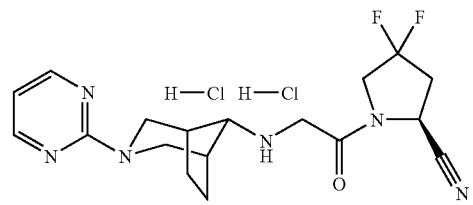

a.) tert-Butyl(3-pyrimidin-2-yl-3-azabicyclo[3.2.1]oct-8-yl)-endo-carbamate

In general formula (V) the meaning of R and B are as defined above, Y represents tert-butoxycarbonyl group.

(i) tert-Butyl(3-benzyl-3-azabicyclo[3.2.1]oct-8-yl)-endo-carbamate

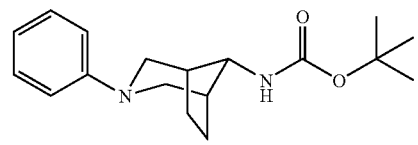

From 1.0 g (4.6 mmole) of 3-benzyl-3-azabicyclo[3.2.1]octan-8-endo-amine obtained in step 2/a./(ii) with di-tert-butyl dicarbonate, according to step 2/a./(iii) 1.02 g (70%) of the title product is obtained. M.p.: 127-129° C. $^1$H-NMR (DMSO-d,): 1.37 (s, 9H), 1.53-1.57 (m, 2H), 1.70 (m, 2H), 2.03 (s, 2H), 2.07 (d, 2H), 2.58 (dd, 2H), 3.24 (d, 1H), 3.44 (d, 2H), 6.60 (s, 1H), 7.12-7.32 (m, 5H). (MH$^+$)=317

(ii) tert-Butyl 3-azabicyclo[3.2.1]oct-8-yl-endo-carbamate

Following the method described in step 4/a./(iv), from 1.0 g (3.2 mmole) of tert-Butyl (3-benzyl-3-azabicyclo[3.2.1]oct-8-yl)-endo-carbamate after debenzylation 0.71 g (98%) of title product is obtained. (MH$^+$)=227.

(iii) tert-Butyl(3-pyrimidin-2-yl-3-azabicyclo[3.2.1]oct-8-yl)-endo-carbamate

Following the method described in step 4/a./(v) from 0.7 g (3.1 mmole) of tert-butyl 3-azabicyclo[3.2.1]oct-8-yl-endo-carbamate with 2-chloropyrimidine 0.87 g (92%) of title product is obtained in the form of an oil. (MH$^+$)=305.

b.) 3-(Pyrimidin-2-yl)-3-azabicyclo[3.2.1]octan-8-endo-amine

In general formula (II) the meaning of R and B are as defined above.

Following the method described in step 4/b.) starting from 0.87 g (2.9 mmole) of tert-butyl(3-pyrimidin-2-yl-3-azabicyclo[3.2.1]oct-8-yl)-endo-carbamate, after hydrolysis 0.49 g (83%) of title product is obtained. (MH$^+$)=205.

c.) (2S)-4,4-difluoro-1-[N-(3-pyrimidin-2-yl-3-azabicyclo[3.2.1]oct-8-yl) endo-aminoacetyl]pyrrolidine-2-carbonitrile dihydrochloride Following the method described in step 4/c.) from 204 mg (1.0 mmole) of 3-(pyrimidin-2-yl)-3-azabicyclo[3.2.1]octan-8-endo-amine and 208 mg (1 mmole) (2S)-1-(chloro-acetyl)-4,4-difluoropyrrolidine-2-carbonitrile the title product is obtained in the form of hydrochloride salt. Yield: 152 mg (34%), m.p.>300° C. $^1$H-NMR (DMSO-d$_6$): 1.44 (d, 2H), 1.98 (m, 2H), 2.67 (s, 2H), 2.86-3.00 (m 4H), 4.09-4.21 (m, 4H), 4.38-4.48 (m, 3H), 5.21 (dd, 1H), 6.71 (t, 1H), 8.39 (d, 2H), 9.11 (d, 2H). (MH$^+$)=377.

EXAMPLE 6

(2S)-4,4-difluoro-1-[N-(3-methyl-8-pyrimidin-2-yl-8-azabicyclo[3.2.1]oct-3-yl)exo-aminoacetyl]pyrrolidine-2-carbonitrile dihydrochloride In general formula (I) R stands for pyrimidin-2-yl group, B stands for the group of formula (5), Z stands for the group of formula (A).

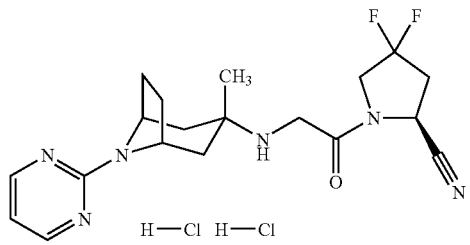

a.) N-(3-methyl-8-pyrimidin-2-yl-8-azabicyclo[3.2.1]oct-3 exo-yl)acetamide

In general formula (V) the meaning of R and B are as defined above, Y represents acetyl group.

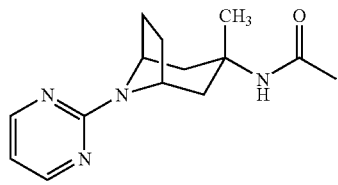

(i) 8-Benzyl-3-methyl-8-azabicyclo[3.2.1]octan-3-exo-ol

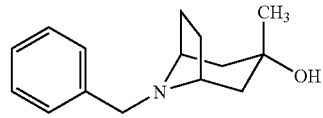

To the solution of 16.00 g (74 mmole) of 8-benzyl-8-azabicyclo[3.2.1]octan-3-one (J. C. S. Perkin I. 1997, 1307) in 270 ml of dry tetrahydrofurane, under nitrogen atmosphere are dropped 38 ml (330 mmole) of methyl magnesium bromide, at −20° C. with syringe. The reaction mixture is stirred at −20° C. for 30 minutes, and then allowed to warm up to room temperature and stirring is continued for 16 hours. To the mixture 900 ml of saturated ammonium chloride solution and 300 ml of diethyl ether are added. After mixing and separation the aqueous phase is extracted with 3×100 ml of dichloromethane, the dichloromethane phase is washed with 100 ml of saturated sodium chloride. The combined organic phase is dried over sodium sulphate and evaporated. The residue is chromatographed on silica gel (chloroform). The product is 5.95 g (35%) oily material. (MH$^+$)=232.

(ii) N-(8-benzyl-3-methyl-8-azabicyclo[3.2.1]oct-3-exo-yl)acetamide

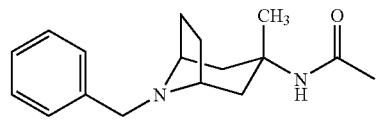

3.0 g (13 mmole) of 8-benzyl-3-methyl-8-azabicyclo [3.2.1]octan-3-exo-ol are dissolved in 15 ml of acetonitrile. To the solution, carefully, under cooling and stirring, 12.2 ml of concentrated sulphuric acid (t<30° C.) is dropped, and the mixture is stirred at room temperature for 16 hours. The reaction mixture is poured onto 100 g of ice. The pH of the solution is adjusted to pH=10 with 50% potassium hydroxide. The mixture is extracted with dichloromethane; the extract is washed with concentrated sodium chloride solution, dried over sodium sulphate and evaporated. The residue is crystallised from the mixture of n-hexane and ether, to obtain 2.11 g (59%) of white crystalline material. M.p.: 151-155° C. (MH$^+$)= 273.

(iii) N-(3-methyl-8-azabicyclo[3.2.1]oct-3-exo-yl)acetamide

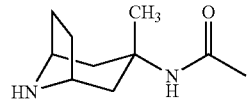

2.10 g (7.7 mmole) of N-(8-benzyl-3-methyl-8-azabicyclo [3.2.1]oct-3-exo-yl)acetamide are hydrogenated as described in step 4/a./(iv). After debenzylation 1.20 g (86%) of the title product is obtained. M.p.: 63-65° C. (MH$^+$)=183.

(iv) N-(3-methyl-8-pyrimidin-2-yl-8-azabicyclo[3.2.1] oct-3-exo-yl)acetamide 1.20 g (6.6 mmole) of (3-methyl-8-azabicyclo[3.2.1]oct-3-exo-yl)acetamide, 0.76 g (6.6 mmole) of 2-chloropyrimidine and 1.18 ml (7.9 mmole) of DBU are heated in n-pentanol under reflux conditions for 8 hours. The reaction mixture is worked-up as described in step 4/a./(v) to obtain 0.89 g (52%) of white crystalline material. M.p.: 175-176° C. (MH⁺)=261.

b.) 3-Methyl-8-pyrimidin-2-yl-8-azabicyclo[3.2.1]octan-3-exo-amine

In general formula (II) the meaning of R and B are as defined above.

0.89 g (3.4 mmole) of N-(3-methyl-8-pyrimidin-2-yl-8-azabicyclo[3.2.1]oct-3-exo-yl)acetamide are refluxed in 35 ml of 2N hydrochloric acid for 16 hours. After cooling the reaction mixture is made alkaline (pH=11) with 20% sodium hydroxide solution and extrated with 20 ml of dichloromethane. The extract is dried over sodium sulphate and evaporated. The residue is suspended in diethyl ether, filtered; the mother liquor is evaporated, to obtain 130 mg (18%) of the product in the form of pale-yellow oil. (MH⁺)=219.

c.) (2S)-4,4-difluoro-1-[N-(3-methyl-8-pyrimidin-2-yl-8-azabicyclo[3.2.1]oct-3-yl)exo-aminoacetyl]pyrrolidine-2-carbonitrile dihydrochloride Following the method described in step 4/c.), from 110 mg (0.5 mmole) of 3-methyl-8-pyrimidin-2-yl-8-azabicyclo[3.2.1]oct-3-yl-exo-amine and 104 mg (0.5 mmole) of (2S)-1-(chloroacetyl)-4,4-difluoropyrrolidine-2-carbonitrile 59 mg (30%) of white, crystalline product is isolated. M.p.: 169-172° C. ¹H-NMR (400 MHz, DMSO-d₆): δ 0.81 (s, 3H), 1.62-1.73 (m, 5H), 1.80 (m, 2H), 2.18 (d, 2H), 2.79-(m, 2H), 3.37-3.45 (m, 2H), 4.04 (ddd, 1H), 4.30 (ddd, 1H), 4.55 (m, 2H), 5.09 (dd, 1H), 6.57 (t, 1H), 8.32 (d, 2H). (MH⁺)=391.

The following compounds of general formula (I) are prepared according to example 1-6 in the Table 1.

TABLE 1

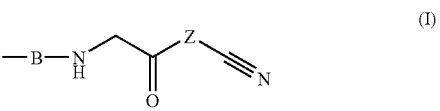

(I)

| Example | R | B | Z | Melting point, composition |
|---|---|---|---|---|
| 7 | 2-pyrimidinyl | (1) | (B) | 151-154° C. |
| 8 | 2-pyrimidinyl | (1) | (D) | 75-78°0 C. |
| 9 | 2-pyrimidinyl | (1) | (E) | 205-207° C. (trihydrochloride) |
| 10 | 3-methyl-1,2,4-triazin-yl | (1) | (A) | 208° C. (trihydrochloride) |
| 11 | methylpyrazinyl | (1) | (A) | 227-228° C. (dihydrochloride) |
| 12 | 4-cyanophenyl | (1) | (A) | 205-208° C. (trihydrochloride) |
| 13 | 4-cyanophenyl | (1) | (A) | 220-221° C. (trihydrochloride) |
| 14 | 6-methyl-5-trifluoromethylpyridin-2-yl | (1) | (A) | 220° C. (trihydrochloride) |
| 15 | 6-methyl-5-trifluoromethylpyridin-2-yl | (1) | (B) | 218° C. (trihydrochloride) |
| 16 | 2,4-dimethylpyridin-yl | (1) | (A) | 233-235° C. (dihydrochloride) |
| 17 | 2,4-dimethylpyridin-yl | (1) | (C) | 90-92° C. (trihydrochloride) |
| 18 | 2-methylthiazol-yl | (1) | (A) | 248-249° C. (trihydrochloride) |
| 19 | 1-ethyl-5-methylpyrazol-yl | (1) | (A) | 209-212° C. (trihydrochloride) |
| 20 | 3,5-dimethylisoxazol-yl | (1) | (A) | 198-199° C. (×2.5 HCl) |
| 21 | 3,5-dimethylisoxazol-yl | (1) | (D) | 192-195° C. (trihydrochloride) |

TABLE 1-continued $$R-B-NH-CH_2-C(=O)-Z-C\equiv N \quad (I)$$

| Example | R | B | Z | Melting point, composition |
|---|---|---|---|---|
| 22 | quinolin-2-ylmethyl | (1) | (A) | 241-244° C. (trihydrochloride) |
| 23 | quinolin-2-ylmethyl | (1) | (B) | 153-154° C. (trihydrate) |
| 24 | [1,2,4]triazolo[1,5-a]pyridin-2-ylmethyl | (1) | (A) | 222-224° C. (trihydrochloride) |
| 25 | [1,2,4]triazolo[1,5-a]pyridin-2-ylmethyl | (1) | (B) | 86-88° C. (monohydrate) |
| 26 | [1,2,4]triazolo[1,5-a]pyridin-2-ylmethyl | (1) | (D) | 224-227° C. (trihydrochloride) |
| 27 | 4-cyanobenzyl (NC-C6H4-CH2) | (1) | (A) | 226-231° C. (trihydrochloride) |
| 28 | 4-(trifluoromethyl)benzyl (F3C-C6H4-CH2) | (1) | (A) | 226-227° C. (trihydrochloride) |
| 29 | 3-fluorobenzyl | (1) | (A) | 224-228° C. (trihydrochloride) |
| 30 | 3,4,5-trimethoxybenzyl | (1) | (A) | 221-224° C. (trihydrochloride) |
| 31 | pyridin-3-ylmethyl | (1) | (A) | 237-238° C. (trihydrochloride + 1.5 H2O) |
| 32 | pyridazin-3-ylmethyl | (1) | (A) | 242-243° C. (pentahydrochloride) |
| 33 | pyridazin-3-ylmethyl | (1) | (D) | 241-242° C. (trihydrochloride-dihydrate) |
| 34 | thiazol-2-ylethyl | (1) | (A) | 225-228° C. (trihydrochloride) |
| 35 | 4-chlorophenacyl | (1) | (A) | 178-180° C. (hydrochloride-hydrate) |
| 36 | 4-chlorophenacyl | (1) | (D) | 185° C. (hydrochloride-dihydrate) |
| 37 | 3-fluorophenacyl | (1) | (A) | 212-214° C. (hydrochloride-dihydrate) |
| 38 | 4-phenyl-3-buten-2-on-yl | (1) | (A) | 191-193° C. (dihydrochloride-hidrate) |
| 39 | 2-acetylthiophen-yl | (1) | (A) | 215-216° C. (hydrochloride-hydrate) |
| 40 | pyrimidin-2-ylmethyl | (2) | (C) | 149-152° C. (dihydrochloride) |
| 41 | pyrimidin-2-ylmethyl | (3) | (C) | 154-155° C. (hydrochloride) |
| 42 | 6-cyanopyridazin-3-ylmethyl | (3) | (A) | 157-160° C. (hydrochloride) |
| 43 | pyrimidin-2-ylmethyl | (4) | (A) | 168-170° C. (dihydrochloride) |

TABLE 1-continued (I) R—B—NH—CH₂—C(O)—Z—CN

| Example | R | B | Z | Melting point, composition |
|---|---|---|---|---|
| 44 | 6-methyl-3-cyanopyridazin-3-yl (NC-pyridazine-CH₃) | (4) | (A) | 169-171° C. (dihydrochloride) |
| 45 | 2-methylpyrimidin-4-yl | (4) | (C) | 153-155° C. (hydrochloride) |

Following procedures outlined for Examples 1/a.) the compounds of the general formula (V)—wherein B is a group of formula (1)—listed in the Table 2 were prepared.

TABLE 2

(V) R—NH—(adamantyl)—NH—C(O)—O—C(CH₃)₃

| Example | R | Melting point |
|---|---|---|
| 2.1. | 3-methyl-1,2,4-triazin-6-yl | 191-193° C. |
| 2.2. | 3-methylpyrazin-2-yl | 169-171° C. |
| 2.3. | 4-cyanophenyl-methyl | 184-186° C. |
| 2.4. | 6-methyl-3-cyanopyridin-5-yl | 169-171° C. |
| 2.5. | 6-methyl-3-trifluoromethylpyridin-5-yl | 191-192° C. |
| 2.6. | 6-methyl-3-cyanopyridin-5-yl | 149-152° C. |
| 2.7. | 6-methyl-3-trifluoromethylpyridazin-3-yl | 154-155° C. |
| 2.8. | 2,4-dimethylpyridin-6-yl | 175-177° C. |
| 2.9. | 2-methylthiazol-5-yl | 173–175° C. |
| 2.10. | 1-ethyl-5-methylpyrazol-3-yl | 115-118° C. |
| 2.11. | 3-methyl-5-methylisoxazol-4-yl | 182-183° C. |
| 2.12. | 2-methylquinolin-3-yl | 173-175° C. |
| 2.13. | 2-methyl[1,2,4]triazolo[1,5-a]pyridin-6-yl | 184-186° C. |

Following procedures outlined for Examples 1/b.), 2/a.) and 3/a.) the compounds of the general formula (II)—wherein B is a group of formula (1)—listed in the Table 3 were prepared.

TABLE 3
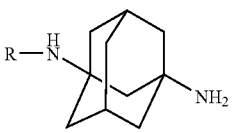
(II)
| Example | R | Characterisation (M.p. or aromtic protons by ¹H-NMR[DMSO-d₆]) |
|---|---|---|
| 3.1. | 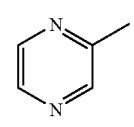 | 8.20 (d, 1H), 8.51 (d, 1H) |
| 3.2. | 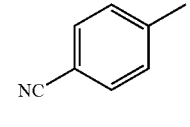 | 7.54 (d, 1H), 7.83 (dd, 1H), 7.87 (d, 1H) |
| 3.3. | 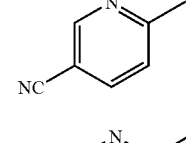 | 6.72 (d, 2H), 7.31 (d, 2H) |
| 3.4. | 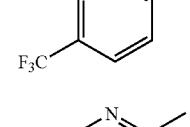 | 6.53 (d, 1H), 7.55 (dd, 1H), 8.30 (d, 1H) |
| 3.5. | 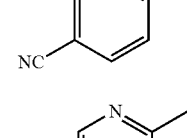 | 114-115° C. |
| 3.6. | 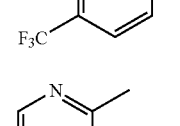 | 149-152° C. |
| 3.7. | 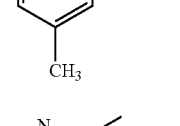 | 154-155° C. |
| 3.8. | 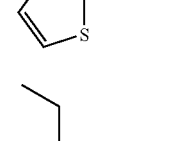 | 115-117° C. |
| 3.9. | 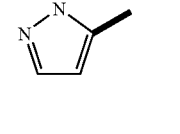 | 6.52 (d, 1H), 6.95 (d, 1H) |
| 3.10. | 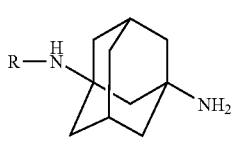 | 1.15 (t, 3H), 3.87 (q, 2H), 5.52 (d, 1H), 7.09 (d, 1H) |
| 3.11. | 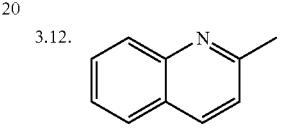 | 2.19 (s, 3H), 5.71 (s, 1H) |
| 3.12. | 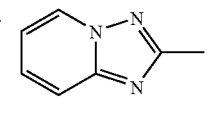 | 135-137° C. |
| 3.13. | 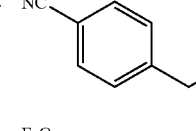 | 6.84 (t, 1H), 7.37 (m, 2H), 8.56 (d, 1H) |
| 3.14. | 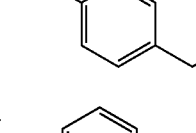 | 108-112° C. |
| 3.15. | 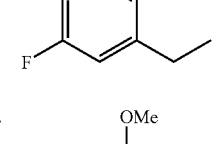 | 7.59 (dd, 4H) |
| 3.16. | 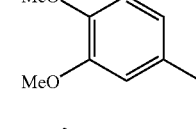 | 7.26 (m, 1H), 7.49 (t, 2H), 7.63 (d, 2H) |
| 3.17. | 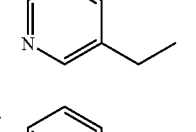 | 3.66 (s, 3H), 3.81 (s, 6H), 7.11 (s, 2H) |
| 3.18. | 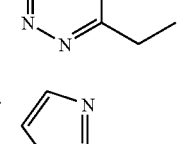 | 7.30 (dd, 1H), 7.72 (d, 1H), 8.39 (d, 2H), 8.50 (s, 1H) |
| 3.19. | 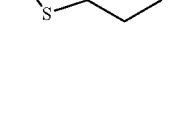 | 7.60 (dd, 1H), 7.73 (d, 1H), 9.06 (d, 1H) |
| 3.20. | | 7.50 (d, 1H), 7.65 (d, 1H) |

TABLE 3-continued

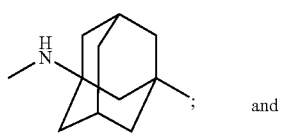
(II)

| Example | R | Characterisation (M.p. or aromtic protons by ¹H-NMR[DMSO-$d_6$]) |
|---|---|---|
| 3.21. | 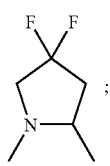 (4-Cl-phenyl-C(O)-) | 7.46 (dd, 2H), 7.77 (dd, 2H) |
| 3.22. | (3-F-phenyl-C(O)-) | 7.32 (m, 1H), 7.48 (m, 1H), 7.60 (m, 2H) |
| 3.23. | (cinnamoyl) | 6.60 (s, 1H), 6.68 (s, 1H), 7.34 (m, 3H), 7.50 (m, 2H |
| 3.24. | (thiophene-2-C(O)-) | 7.10 (t, 1H), 7.69 (dd, 1H), 7.80 (dd, 1H) |

We claim:

1. A compound of formula (I)

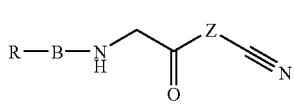
(I)

wherein

R is selected from a group consisting of:
a nitrogen-containing mono- or bicyclic aromatic moiety selected from the group consisting of pyridyl, pyridazinyl, pyrimidinyl, pyrazinyl, imidazolyl, pyrazolyl, thiazolyl, isothiazolyl, oxazolyl, isoxazolyl, oxadiazolyl, tetrazolyl, triazinyl, quinolinyl, isoquinolinyl, cinnolinyl, phthalazinyl, quinazolinyl, quinoxalinyl, benzimidazolyl, indazolyl, benzothiazolyl, benzisothiazolyl, benzoxazolyl or benzisoxazolyl wherein each nitrogen-containing mono- or bicyclic aromatic moiety is optionally mono- or disubstituted with the same or different groups selected from $C_{1-4}$alkyl, $C_{1-4}$alkoxy, $C_{2-5}$alkoxycarbonyl, halogen, trihalogenomethyl, methylthio, nitro, carboxamido or cyano;

B is:

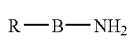
(1)

and

Z is formula (A):

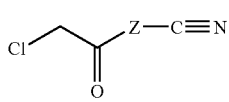
(A)

or an isomer or pharmaceutically acceptable salt thereof.

2. The compound of the formula (I) which is:
(2S)-4,4-difluoro-1-{N-[3-(pyrimidin-2-ylamino)-1-adamantyl]glycyl}pyrrolidine-2-carbonitrile;
6-[(3-{[2-(2-cyano-(2S)-4,4-difluoropyrrolidin-1-yl)-2-oxoethyl]amino}-1-adamantyl) amino]nicotinonitrile;
(2S)-4,4-difluoro-1-[N-(3-{[5-(trifluoromethyl)pyridin-2-yl]amino}-1-adamantyl)glycyl]pyrrolidine-2-carbonitrile;
(2S)-4,4-difluoro-1-{N-[3-(1,3-thiazol-2-ylamino)-1-adamantyl]glycyl}pyrrolidine-2-carbonitrile;
(2S)-1-(N-{3-[(1-ethyl-1H-pyrazol-5-yl)amino]-1-adamantyl}glycyl)-4,4-difluoropyrrolidine-2-carbonitrile;
(2S)-4,4-difluoro-1-(N-{3-[(5-methylisoxazol-3-yl)amino]-1-adamantyl}glycyl)pyrrolidine-2-carbonitrile;
(2S)-4,4-difluoro-1-{N-[3-(quinolin-2-ylamino)-1-adamantyl]glycyl}pyrrolidine-2-carbonitrile;
(2S)-4,4-difluoro-1-{N-[3-([1,2,4]triazolo[1,5-α]pyridin-2-ylamino)-1-adamantyl]glycyl}pyrrolidine-2-carbonitrile;
(2S)-4,4-difluoro-1-(N-{3-[(pyridin-3-ylmethyl)amino]1-adamantyl}glycyl)pyrrolidine-2-carbonitrile;
(2S)-4,4-difluoro-1-(N-{3-[(pyridazin-3-ylmethyl)amino]1-adamantyl}glycyl)pyrrolidine-2-carbonitrile;
(2S)-4,4-difluoro-1-(N-{3-[(1,3-thiazol-2-ylmethyl)amino]-1-adamantyl}glycyl)pyrroliine-2-carbonitrile;
or an isomer or pharmaceutically acceptable salt thereof.

3. A pharmaceutical composition comprising a compound of claim 1 and a pharmaceutically acceptable carrier.

4. A process for preparing a compound of Formula I of claim 1 comprising the steps of:
a) reacting a compound of formula (II)

R—B—NH₂ (II)

with a compound of formula (III)

(III)

wherein the meanings of R, B and Z are as defined in claim 1; and b) isolating the resulting compound of the general formula (I) or its salt from the reaction mixture.

5. A method of treating non-insulin dependent diabetes mellitus in a patient in need thereof comprising administering a therapeutically effective amount of a compound of claim 1.

* * * * *

UNITED STATES PATENT AND TRADEMARK OFFICE
CERTIFICATE OF CORRECTION

PATENT NO. : 7,652,021 B2  Page 1 of 1
APPLICATION NO. : 11/364154
DATED : January 26, 2010
INVENTOR(S) : Aranyi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 70 days.

Signed and Sealed this

Twenty-third Day of November, 2010

David J. Kappos
*Director of the United States Patent and Trademark Office*